United States Patent [19]

Padmapriya et al.

[11] Patent Number: 5,801,256
[45] Date of Patent: Sep. 1, 1998

[54] METHOD FOR THE SYNTHESIS OF 8-C-β-D [2'-O-(E)-CINNAMOYL]GLYCOPYRANOSYL-2-[2-HYDROXY]PROPYL-7-METHOXY-5-METHYLCHROMONE

[75] Inventors: Abeysinghe A. Padmapriya, Boulder; Belaid Mahiou, Westminster, both of Colo.

[73] Assignee: Univera Pharmaceuticals, Inc., Broomfield, Colo.

[21] Appl. No.: 858,741

[22] Filed: May 19, 1997

[51] Int. Cl.$^6$ ................................................. C07D 311/22
[52] U.S. Cl. ............................................................ 549/401
[58] Field of Search ................................................. 549/401

[56] References Cited

U.S. PATENT DOCUMENTS 4,656,029  4/1987  Grollier et al. .
5,675,000  10/1997  Waller et al. ............................ 536/128

FOREIGN PATENT DOCUMENTS

96/40182  12/1996  WIPO .

OTHER PUBLICATIONS

Davis et al. (1986) Proceedings of the Pa. Acad. Sci. 60:67.
Davis et al. (1989) J. Am. Podiatric Med. Assoc. 79:395.
Davis et al. (1994) J. Am. Podiatric Med. Assoc. 84:77.
Fink (1991) Clinical and Experimental Rheumatology 9:9.
Fries (1991) Journal of Rheumatology 18:6.
Gilfoil and Klavins (1965) Amer. J. Physiol. 208:867.
Gramatica et al. (1982) Tetrahedron Letters 23:2423.
Hart et al. (1988) Journal of Ethnopharmacology 23:61.
Hirata and Suga (1977) Z. Naturforsch 32c:731.
Holdsworth (1972) *Chromones in Aloe Species, Part I—Aloesin*, PM 19(4):322.
Holdsworth (1972) *Chromones in Aloe Species, Part II—Aloesone*, PM 22(1):54.
Paulus (1985) Arthritis and Rheumatism 28:1168.
Speranza et al. (1985) Phytochemistry 24:1571.
Speranza et al. (1986) Phytochemistry 25:2219.
Strickland et al. (1994) J. Investigative Dermatology 102:197.
van Wyk et al. (1995) Planta Med. 61:250.
Yagi et al. (1987) Planta medica 515.

*Primary Examiner*—Michael G. Ambrose
*Attorney, Agent, or Firm*—Swanson & Bratschun LLC

[57] ABSTRACT

The present invention discloses a two-step method for the preparation of 8-C-β-D-[2'-O-(E)-cinnamoyl] glycopyranosyl-2-[2-hydroxy]propyl-7-methoxy-5-methylchromone (the "540 compound) from the readily available 5-methylchromone, Aloesin.

8 Claims, 1 Drawing Sheet

Aloesone

Aloesin

Aloeresin A

"540" Compound

Aloeresin C

Aloeresin D

METHOD FOR THE SYNTHESIS OF 8-C-β-D [2'-O-(E)-CINNAMOYL]GLYCOPYRANOSYL-2-[2-HYDROXY]PROPYL-7-METHOXY-5-METHYLCHROMONE

FIELD OF THE INVENTION

The present invention relates generally to a method for the synthesis of an anti-inflammatory and epithelial growth factor-inhibiting compound isolated from the *Aloe barbadensis* plant. Specifically, this invention describes the synthesis of C-glycosylated 5-methylchromone, 8-C-β-D-[2'-O-(E)-cinnamoyl]glycopyranosyl-2-[2-hydroxy]propyl-7-methoxy-5-methylchromone, which has a molecular formulae of $C_{29}H_{32}O_{10}$, and is referred to herein as the "540 compound."

BACKGROUND OF THE INVENTION

Aloe is an intricate plant which contains many biologically active substances. (Cohen et al. in *Wound Healing/Biochemical and Clinical Aspects*, 1st ed. WB Saunders, Philadelphia (1992)). Over 300 species of Aloe are known, most of which are indigenous to Africa. Studies have shown that the biologically active substances are located in three separate sections of the aloe leaf—a clear gel filet located in the center of the leaf, in the leaf rind or cortex of the leaf and in a yellow fluid contained in the pericyclic cells of the vascular bundles, located between the leaf rind and the internal gel filet, referred to as the latex. Historically, Aloe products have been used in dermatological applications for the treatment of burns, sores and other wounds. These uses have stimulated a great deal of research on identifying compounds from Aloe that have clinical efficacy, particularly anti-inflammatory activity. (See, e.g., Grindlay and Reynolds (1986) J. of Ethnopharmacology 16:117–151; Hart et al. (1988) J. of Ethnopharmacology 23:61–71). As a result of these studies there have been numerous reports of Aloe compounds having diverse biological activities, including anti-tumor activity, anti-acid activity (Hirata and Suga (1977) Z. Naturforsch 32c:731–734), anti-diabetic activity, tyrosinase inhibiting activity (Yagi et al. (1987) Planta medica 515–517) and antioxidant activity (International Application Serial No. PCT/US95/07404, published Dec. 19, 1996, publication number WO 96/40182). Aloe products are also used extensively in the cosmetic industry to protect skin against ultraviolet light. (Strickland et al. (1994) J. Invest. Dermatol. 102:197; Grollier et al. U.S. Pat. No. 4,656,029, issued Apr. 7, 1987).

One class of biologically active compounds that have been isolated from Aloe are the 5-methylchromones, which have the following general structure and conventional numbering:

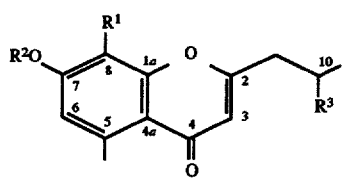

wherein $R^1$ is H, glucose or a derivative of glucose, $R^2$ is H, $CH_3$, or glucose and $R^3$ is OH or =O. (See Holdsworth (1972) *Chromones in Aloe Species, Part I - Aloesin*, PM 19(4):322–325; Holdsworth (1972) *Chromones in Aloe Species, Part II - Aloesone*, PM 22(1):54–58; Speranza et al. (1986) Phytochemistry 25:2219–2222; Speranza et al. (1985) Phytochemistry 24:1571–1573; Gramatica et al. (1982) Tetrahedron Letters 23:2423–2424). A list of some of the 5-methylchromones that have been isolated from Aloe to date is set forth in FIG. 1.

Inflammation is a localized protective response elicited by injury or destruction of tissue resulting from physical trauma, microbial invasion or immune disorders, such as rheumatoid arthritis. Although inflammation is vital to the healing process, if uncontrolled, it can lead to more serious conditions. (Davis et al. (1986) Pa. Acad. Sci. 60:67; Gilfoil and Klavins (1965) Amer. J. Physiol. 208:867). Rheumatoid arthritis, for example, is a chronic and progressive inflammatory disease which affects connective tissue. It is characterized by inflammation in multiple joints and is a major cause of disability.

Current treatment for inflammation usually involves the use of anti-inflammatory agents, such as, steroids or non-steroidal aspirin-like drugs. Many of the anti-inflammatory agents currently on the market have serious side effects that significantly limit their usefulness. Aspirin-like drugs, for example, cause gastropathy, which accounts for numerous hospitalizations and deaths in the United States each year. (Fries (1991) J. Rheumatol. 18:6–10; Paulus (1985) Arthritis Rheum. 28:1168–1169). Additionally, these compounds only provide symptomatic relief and do not reduce the underlying pathology of the disease. Steroids, on the other hand, can lessen both the tissue destruction and the symptoms resulting from inflammation, however, steroids frequently cause suppression of pituitary-adrenal function, immune suppression and seriously disturb fluid and electrolyte balance. In children, steroid use can prevent growth and can even cause death. (Fink (1991) Clin. Exper. Rheum. 2:9–13).

The anti-inflammatory activity of Aloe compounds has been extensively investigated. Studies by Davis et al. have shown that Aloe vera, a term used to describe the extract obtained from processing the entire leaf, not only reduces inflammation, but also improves wound healing. (Davis et al. (1994) J. Am. Podiatric Med. Assoc. 84:77–81; Davis et al. (1989) J. Am. Podiatric Med. Assoc. 79:395–397). The anti-inflammatory/wound healing ability of Aloe vera has been attributed to a growth factor-like substance that activates the wound healing and inflammation reduction processes. (Davis et al. (1994) J. Am. Podiatric Med. Assoc. 84:77–81, Davis et al. (1989) J. Am. Podiatric Med. Assoc. 79:395–397). In U.S. application Ser. Nos. 08/391,139, filed Feb. 21, 1995 (now abandoned) and 08/686,270, filed Jul. 25, 1996, each of which is incorporated herein by reference and entitled "Cinnamoyl-C-Glycoside Chromone Isolated from *Aloe barbadensis*," it was reported that the cinnamoyl-C-glycoside 5-methylchromone, 8-C-β-D-[2'-O-(E)-cinnamoyl]glycopyranosyl-2-[2-hydroxy]propyl-7-methoxy-5-methylchromone (the "540 compound"), has anti-inflammatory activity comparable to hydrocortisone.

To date, little work has been done to modify compounds isolated from Aloe. For the purpose of characterizing Aloeresin D (FIG. 1), Speranza et al. prepared the 7-O-methyl-10-hydroxy derivative of Aloesin by methylation of the 7-hydroxy group with diazomethane, followed by reduction of the carbonyl group at C10 with NaBH₄. (Speranza et al. (1986) Phytochemistry 25:2219, 2222). Additionally, little work has been done in the area of synthesis of these compounds. Currently there is no reported synthesis of the 540 compound.

SUMMARY OF THE INVENTION

The present invention describes a method for the synthesis of the C-glycosylated 5-methylchromone, 8-C-β-D-[2'-O-(E)-cinnamoyl] glycopyranosyl-2-[2-hydroxy]propyl-7-methoxy-5-methylchromone (the "540 compound") (3) from the readily available 5-methylchromone, Aloesin (1). (See Holdsworth (1972) *Chromones in Aloe Species, Part I - Aloesin*, PM 19(4):322–325). More specifically, the invention provides a method for the synthesis of the 540 compound (3) comprising the steps of: reduction of the C10 carbonyl of Aloesin (1) to provide Aloesinol (2), esterification of the 2'-OH of Aloesinol (2) with cinnamoyl chloride to provide the 2'-O-cinnamoyl ester followed by methylation of the hydroxy group at C7 to yield the 540 compound. Because Aloesin (1) is present in much greater quantities in Aloe than the 540 compound (0.2% vs. 0.01% on a dry weight basis, respectively) and is easily isolated and purified, the method of this invention provides a much more efficient and cost effective means to obtain the 540 compound.

It is to be understood that both the foregoing general description and the following detailed description are exemplary and explanatory only and are not restrictive of the invention as claimed.

DETAILED DESCRIPTION OF THE INVENTION

The present invention includes a method for the synthesis of the C-glycosylated 5-methylchromone, 8-C-β-D-[2'-O-(E)-cinnamoyl] glycopyranosyl-2-[2-hydroxy]propyl-7-methoxy-5-methylchromone. This compound has been isolated from the *Aloe barbadensis* plant and has the following chemical structure:

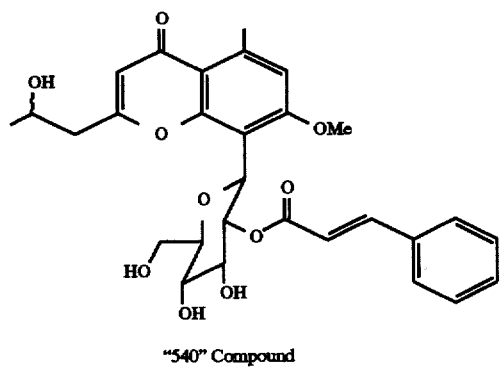

"540" Compound

The 540 compound is present primarily in the leaf rind of the *Aloe barbadensis* plant. The 540 compound exhibits potent anti-inflammatory activity as measured by in vivo assays. This compound has also been shown to inhibit EGF-induced DNA synthesis in in vitro testing in epithelial cell lines. The isolation, purification and structural determination of the 540 compound and its activity are described in detail in related U.S. application Ser. No. 08/391,139, entitled "Cinnamoyl-C-Glycoside Chromone Isolated from *Aloe barbadensis*," filed Feb. 21, 1995 and U.S. application Ser. No. 08/621,178, entitled "Purification of Cinnamoyl-C-Glycoside Chromone," filed Mar. 21, 1996, both of which are incorporated herein by reference in their entirety.

Specifically, the present invention includes a method for the synthesis of the 540 compound starting from the readily available 5-methylchromone Aloesin (1). (See Holdsworth (1972) *Chromones in Aloe Species, Part I - Aloesin*, PM 19(4):322– 325; van Wyk et al. (1994) Planta Med 61:250–253). Aloesin was the first chromone to be isolated from a wide variety of Aloe species. It is one of the main biologically active compounds isolated from leaf exudates and is easily isolated and purified.

Certain terms used to describe the invention herein are defined as follows:

The term "Aloe" refers to the genus of plants found worldwide from the Liliaceae family of which the *Aloe barbadensis* plant is a species.

Figure 1:
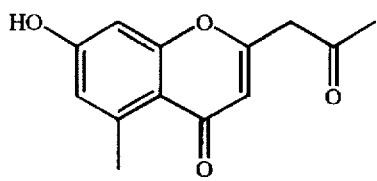
FIG. 1 illustrates the chemical structure of various 5-methylchromones isolated from Aloe.
Figure 1:
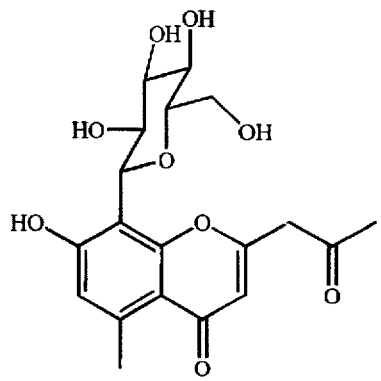
Figure 1:
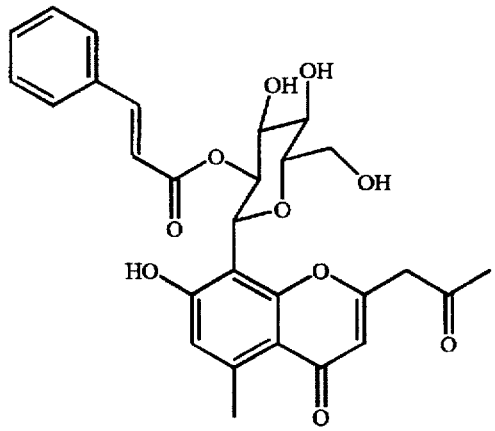
Figure 1:
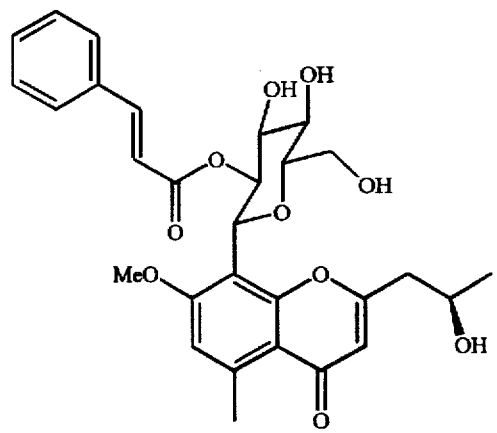
Figure 1:
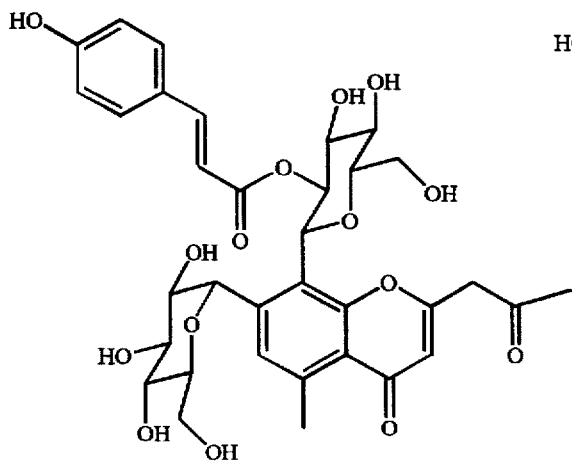
Figure 1:
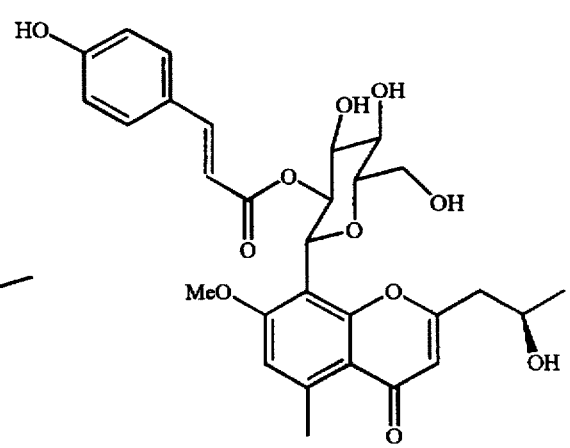

A "5-methylchromone" is one of a group of aromatic compounds having the following structure and conventional numbering:

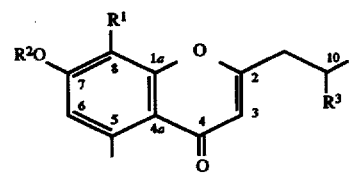

wherein $R^1$ is H, glucose or a derivative of glucose, $R^2$ is H, $CH_3$, or glucose and $R^3$ is OH or =O. A list of 5-methylchromones isolated and characterized to date is set forth in FIG. 1. Most 5-methylchromones have a glucose or a derivative of glucose at C8 and are referred to as "C-glycosylated 5-methylchromones."

The general method of the present invention can be characterized as outlined in Scheme 1. As shown in Scheme 1, reaction of the readily available 5-methylchromone Aloesin (1) (Holdsworth (1972) *Chromones in Aloe Species, Part I - Aloesin*, PM 19(4):322–325; van Wyk et al. (1994) Planta Med 61:250–253) with reducing agents, such as but not limited to metal hydrides, results in the reduction of the C10 carbonyl group to produce the C10 hydroxy 5-methylchromone Aloesinol (2). Examples of metal hydrides which can be used include but are not limited to metal acids, aluminum hydrides, borohydrides and selectides. In a preferred embodiment the C10 carbonyl group of Aloesin (1) is reduced with e.g., NaBH₄, to provide a mixture of diastereomers which is purified by reverse phase chromatography as outlined in the Example section below.

Scheme 1

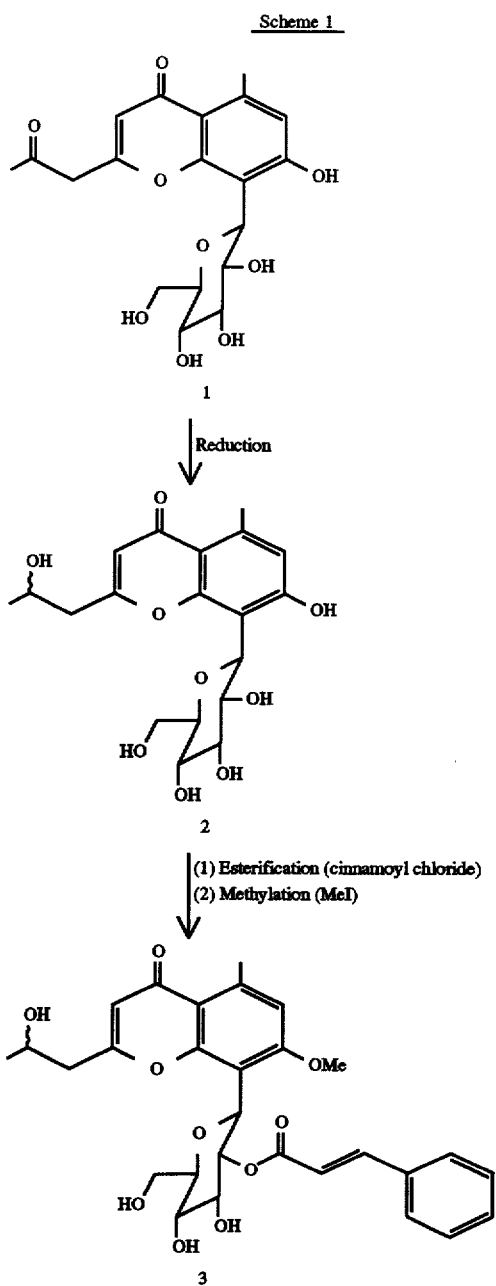

The purified Aloesinol (2) is then treated with an activated cinnamic acid derivative including but not limited to imidazolides, esters, anhydrides, azides, halides and imides in the presence of a base to provide the 2'-O-cinnamoyl ester which is then treated with a methylating agent, preferably methyl iodide to provide the 540 compound (3). In a preferred embodiment the cinnamic acid derivative is cinnamoyl chloride and the base is $Na_2CO_3$.

The following examples are provided for illustrative purposes only and are not intended to limit the scope of the invention.

EXAMPLE

Preparation of 8-C-β-D-[2'-O-(E)-cinnamoyl] glycopyranosyl-2-[2-hydroxy]propyl-7-methoxy-5-methylchromone (Compound 540)

8-C-β-D-[2'-O-(E)-cinnamoyl]glycopyranosyl-2-[2-hydroxy]propyl-7-methoxy-5-methylchromone (compound 540) was synthesized as outlined above in Scheme 1. Briefly, the known and readily available 5-methylchromone Aloesin (1), isolated from Aloe (Holdsworth (1972) *Chromones in Aloe Species, Part I - Aloesin*, PM 19(4):322–325) was reduced with $NaBH_4$ to the C10 hydroxy 5-methylchromone, Aloesinol (2). The Aloesinol (2) was then esterified with cinnamoyl chloride and methylated with methyl iodide to yield the 540 compound.

Preparation of Aloesinol (2).

Scheme 2

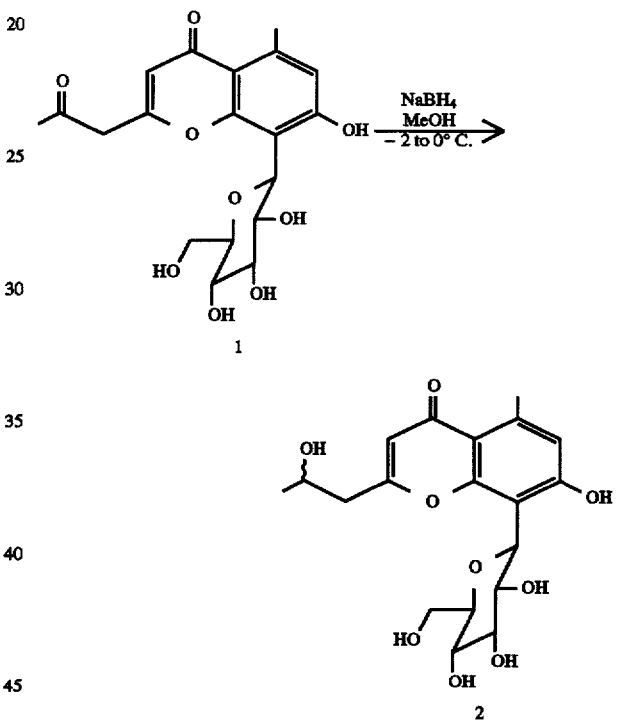

Aloesinol (2) was synthesized by the reduction of Aloesin (1) as follows. A solution of Aloesin (1) (20 g) in methanol (175 mL) was cooled in ice bath at 0° C. followed by the addition of solid sodium borohydride (4 g). The mixture was then removed from the ice bath and stirred for 30 minutes. After 30 minutes the solvent was removed and the residue was dissolved in water (100 mL). The pH of the solution was adjusted to 6.0 (pH paper) with 1N aqueous citric acid. The product was purified by reversed phase HPLC chromatography by elution with 1 L of water followed by aqueous methanol. (Rainin Microsorb mv [86-200-E3] C-18, 100 Å, 3 μm 4.6 mm ID×10 cm L, 100% water (0–2 min.), linear gradient to 100% methanol (2–22 min.), 1 ml/min. flow rate). Fractions containing Aloesinol (2) were collected and concentrated to obtain 18.2 g (90.5% yield) as a light yellow solid, which is a mixture of diastereomers. The HPLC retention time of Aloesinol was 10.36 and 10.49 minutes. The HPLC retention time of Aloesin is 9.73 minutes.

Preparation of 8-C-β-D-[2'-O-(E)-cinnamoyl] glycopyranosyl-2-[2-hydroxy]propyl-7-methoxy-5-methylchromone (540 Compound).

Scheme 3

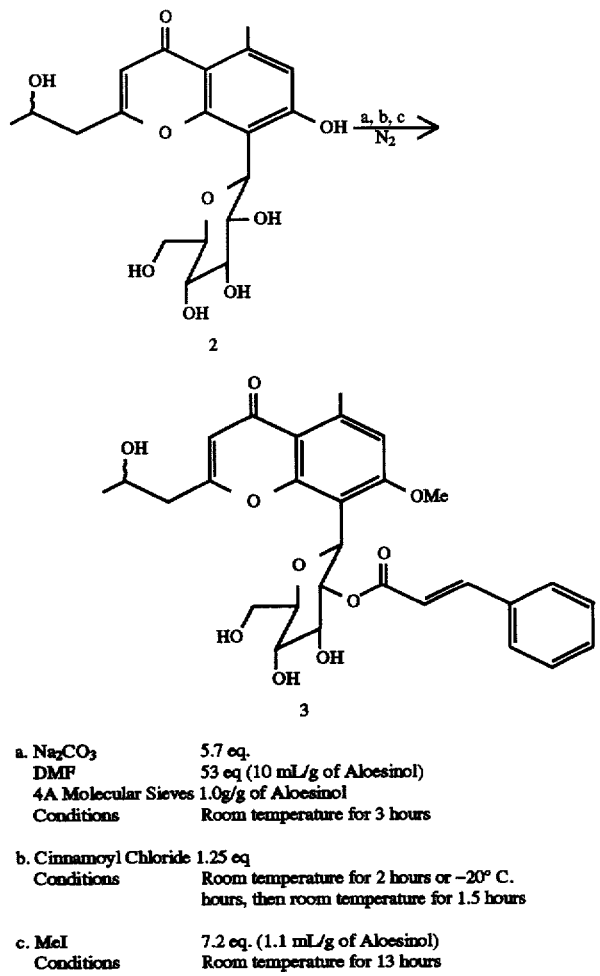

| a. Na₂CO₃ | 5.7 eq. |
| --- | --- |
| DMF | 53 eq (10 mL/g of Aloesinol) |
| 4A Molecular Sieves | 1.0 g/g of Aloesinol |
| Conditions | Room temperature for 3 hours |
| b. Cinnamoyl Chloride | 1.25 eq |
| Conditions | Room temperature for 2 hours or -20° C. hours, then room temperature for 1.5 hours |
| c. MeI | 7.2 eq. (1.1 mL/g of Aloesinol) |
| Conditions | Room temperature for 13 hours |

A solution of 0.5 g of Aloesinol (2) in 5 mL of dry DMF was treated with 0.5 g of 4 Å molecular sieves (Aldrich Chemical Company). The reaction mixture was cooled to 0° C. in an ice bath and stirred for 30 minutes under N₂. After 30 minutes 0.5 g of Na₂CO₃ was added and the mixture was stirred at 0° C. for an additional hour. Cinnamoyl chloride (220 mg) was added and the resulting mixture was stirred for two hours at room temperature. After two hours the reaction mixture was then treated with iodomethane (0.5 mL) and the resulting mixture was stirred under N₂ for 14 hours. The solvent was evaporated and a sample was analyzed by HPLC, as described above. HPLC analysis indicated the presence of compound 540 at 17.10 minutes together with methyl aloesinol and other uncharacterized compounds (eluting at 17–20 minutes). The peak at 17.10 minutes was confirmed to be compound 540 by co-injection with an authentic sample of compound 540.

10 mL of water was added to the reaction mixture and the mixture was extracted with ethyl acetate (3×30 mL). The ethyl acetate layer was dried over MgSO₄ and evaporated to dryness. The residue was purified by flash column chromatography on silica gel using 8% methanol in methylene chloride. The fractions containing compound 540 were collected and concentrated to obtain 110 mg (16% yield) of compound 540 together with 20 mg of an unknown compound (HPLC retention time of about 18 minutes).

We claim:

1. A method for the preparation of 8-C-β-D-[2'-O-(E)-cinnamoyl] glycopyranosyl-2-[2-hydroxy]propyl-7-methoxy-5-methylchromone comprising the steps of:

a. reducing Aloesin to Aloesinol;

b. esterifying Aloesinol; and c. methylating the esterified Aloesinol.

2. The method of claim 1 wherein said Aloesin is reduced with a metal hydride.

3. The method of claim 2 wherein said metal hydride is selected from the group consisting of metal acids, aluminum hydrides, borohydrides and selectrides.

4. The method of claim 2 wherein said metal hydride is NaBH₄.

5. The method of claim 1 wherein said Aloesinol is esterified with a cinnamic acid derivative.

6. The method of claim 5 wherein said cinnamic acid derivative is selected from the group consisting of an imidazolide, ester, anhydride, azide, halide and imide.

7. The method of claim 1 wherein said esterified Aloesinol is methylated with MeI.

8. A method for the preparation of 8-C-β-D-[2'-O-(E)-cinnamoyl] glycopyranosyl-2-[2-hydroxy]propyl-7-methoxy-5-methylchromone comprising the steps of:

a. reducing Aloesin to Aloesinol with a metal hydride;

b. esterifying the Aloesinol with cinnamoyl chloride; and c. methylating the esterified Aloesinol with MeI.

* * * * *